(12) United States Patent
Shutt (10) Patent No.: US 7,030,284 B2
(45) Date of Patent: Apr. 18, 2006

(54) METHOD AND REACTOR SYSTEM FOR CONVERTING OXYGENATE CONTAMINANTS IN AN MTO REACTOR SYSTEM PRODUCT EFFLUENT TO HYDROCARBONS

(75) Inventor: John Richard Shutt, Tervuren (BE)

(73) Assignee: ExxonMobil Chemical Patents Inc., Houston, TX (US)

(*) Notice: Subject to any disclaimer, the term of this patent is extended or adjusted under 35 U.S.C. 154(b) by 641 days.

(21) Appl. No.: 10/224,160

(22) Filed: Aug. 20, 2002

(65) Prior Publication Data

US 2004/0039239 A1    Feb. 26, 2004

(51) Int. Cl.
*C07C 1/00* (2006.01)
*C07C 1/20* (2006.01)

(52) U.S. Cl. .............. 585/314; 585/324; 585/315; 585/733; 585/802; 585/638; 585/639; 585/640

(58) Field of Classification Search ............... 585/314, 585/315, 733, 802, 324, 638, 639, 640
See application file for complete search history.

(56) References Cited

U.S. PATENT DOCUMENTS

| | | | | |
|---|---|---|---|---|
| 3,960,964 A * | 6/1976 | Suggitt et al. | ............ | 564/494 |
| 4,059,648 A | 11/1977 | Derr et al. | ............ | 260/676 |
| 4,071,574 A | 1/1978 | Milstein et al. | ............ | 260/676 |
| 4,080,397 A | 3/1978 | Derr et al. | ............ | 260/676 |
| 4,328,090 A | 5/1982 | Stuckey, Jr. et al. | ............ | 208/44 |
| 4,474,647 A | 10/1984 | Asselineau et al. | ............ | 203/49 |
| 4,482,772 A | 11/1984 | Tabak | ............ | 585/254 |
| 4,499,327 A | 2/1985 | Kaiser | ............ | 585/640 |
| 5,090,977 A | 2/1992 | Strack et al. | ............ | 62/23 |
| 5,714,662 A | 2/1998 | Vora et al. | ............ | 585/640 |
| 5,720,929 A | 2/1998 | Minkkinen et al. | ............ | 422/190 |
| 5,914,433 A | 6/1999 | Marker | ............ | 585/313 |
| 6,121,504 A | 9/2000 | Kuechler et al. | ............ | 585/640 |
| 6,717,025 B1 * | 4/2004 | Risch et al. | ............ | 585/804 |
| 6,764,602 B1 * | 7/2004 | Shutt et al. | ............ | 210/663 |
| 6,855,858 B1 * | 2/2005 | Cheng et al. | ............ | 585/809 |

FOREIGN PATENT DOCUMENTS

EP    0 060 103    4/1985

OTHER PUBLICATIONS

Eng et al., "Integration of the UOP/HYDRO MTO Process into Ethylene Plants," UOP LLC, Des Plaines, Ill., pp. 56-85, (1998).

Weisser et al., "Sulphide Catalysts, Their Properties and Applications," Pergamon Press, Oxford, pp. 150-179, (1973).

* cited by examiner

*Primary Examiner*—Elizabeth D. Wood (57) ABSTRACT

Disclosed is a method and reactor system for converting oxygenate and/or olefin contaminants in a methanol to olefin reactor system product effluent to hydrocarbons, including paraffin compounds, preferably over a sulphided catalyst of the type Nickel or Cobalt combined with Molybdenum or Tungsten. In one embodiment, the oxygenate-containing stream to be hydrogenated comprises one or more of the following streams, alone or in combination: a quench tower bottoms stream, a water absorption unit bottoms stream, a $C_4+$ stream, and/or a $C_5+$ stream.

8 Claims, 2 Drawing Sheets

METHOD AND REACTOR SYSTEM FOR CONVERTING OXYGENATE CONTAMINANTS IN AN MTO REACTOR SYSTEM PRODUCT EFFLUENT TO HYDROCARBONS

FIELD OF THE INVENTION

This invention is to an apparatus and reactor system for converting oxygenate contaminants in a methanol to olefin reactor system product effluent to hydrocarbons. More particularly, the invention is to converting oxygenate contaminants in a $C_4+$ or $C_5+$ fraction, a quench tower bottoms, and/or a water absorption unit bottoms to paraffin hydrocarbons preferably over a sulphided catalyst of the type Nickel or Cobalt combined with Molybdenum or Tungsten.

BACKGROUND

Olefins have been traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred methanol conversion process is generally referred to as a methanol-to-olefin(s) (MTO) process, where methanol is converted to primarily ethylene and/or propylene in the presence of a molecular sieve catalyst.

Undesirable $C_4+$ or $C_5+$ olefins (heavy olefins) can be formed as byproducts of the MTO process. U.S. Pat. No. 5,714,662 to Vora et al. provides a practical use for a $C_3$ and $C_4$ olefin stream separated from an MTO product effluent and for water byproduct formed in the MTO process. More specifically, the Vora et al. patent is directed to a process for producing light olefins from crude methanol. The patent discloses that propylene and butylene fractions from the MTO product effluent can be converted to high octane ether and other high value products. Optionally, butylene from the MTO process can be dimerized and hydrogenated to produce a $C_8$ alkylate having a high octane for use in blending motor gasoline.

Undesirable oxygenate compounds such as alcohols, aldehydes, ketones, esters, acids and ethers in the $C_1$ to $C_6$ range as well as trace quantities of aromatic compounds can also be formed in MTO reactors or in effluent processing. Additionally, a small amount of oxygenate from the feedstock, e.g., methanol or dimethyl ether ("DME"), can pass through the MTO reactor with the product effluent without being converted to desired product. As a result of oxygenate synthesis and/or oxygenate "pass through" in an MTO reactor system, the effluent from an MTO reactor can contain undesirably high concentrations of oxygenate compounds.

Oxygenate and heavy olefin compounds contained in an MTO product effluent can be undesirable for several reasons. For example, in order for an olefin-containing effluent to be suitable for polymerization the effluent should contain, at most, a relatively small amount of oxygenates. Thus, oxygenate separation from the desired light olefins can be required in order to provide an olefin product stream of a sufficient purity for polymerization. Increased investment is required to separate and recover the oxygenates from the desired light olefins.

Additionally, although the relative concentrations of oxygenates and heavy olefins in the product effluent are generally quite low, the total amount of oxygenates and heavy olefins in the effluent on an industrial scale can be enormous. A need exists for providing a use for the oxygenate and heavy olefin compounds which have been separated from the product effluent. That is, it is desirable to provide a practical use for the recovered oxygenate and heavy olefin contaminants so that commercial value can be realized from the oxygenate and heavy olefin contaminants separated from the product effluent.

SUMMARY OF THE INVENTION

The present invention provides a practical use for oxygenate and olefin contaminants in a methanol-to-olefin (MTO) reactor system product effluent. As used herein, "oxygenate" means one or more oxygenated hydrocarbons having at least one oxygen atom and at least one carbon atom. The invention is directed to a method and reactor system for converting oxygenate and/or olefin contaminants in a methanol to olefin reactor system product effluent to hydrocarbons, including mostly paraffins, preferably over a sulphided catalyst of the type Nickel or Cobalt combined with Molybdenum or Tungsten. In one embodiment, the oxygenate-containing stream to be hydrogenated comprises one or more of the following streams, alone or in combination: a quench tower bottoms stream, a water absorption unit bottoms stream, a $C_4+$ stream, and/or a $C_5+$ stream. The resulting $C_4+$ and/or $C_5+$ paraffin compounds can be used in blending motor gasoline, or as a solvent, or as steam cracking feed. Preferably, the oxygenates are concentrated or in admix with a $C_4+$ and/or a $C_5+$ hydrocarbons derived as co-products from an MTO conversion process.

One embodiment of the invention is a method for hydrogenating oxygenate compounds including providing an effluent stream from an oxygenate to olefin reactor system. The effluent stream comprises one or more oxygenates, at least a portion of which are hydrogenated. Optionally, the hydrogenation includes contacting the oxygenates with hydrogen and a catalyst under conditions effective to convert at least a portion of the oxygenates to paraffins.

Another embodiment is directed to a reactor system for converting oxygenate contaminants in an MTO product effluent to paraffins. The reactor system includes a reactor which converts an oxygenate-containing feedstock to an olefin-containing effluent, and a separation system in fluid communication with the reactor. The separation system separates light olefins in the olefin-containing effluent from oxygenate contaminants in the olefin-containing effluent. Optionally, the separation system includes a quench tower, a water absorption unit and/or a distillation unit, each of which forms a overhead stream comprising at least a portion of the light olefins, and a bottoms stream comprising at least a portion of the oxygenate contaminants. The reactor system also includes a hydrogenation unit which receives the oxygenate contaminants from the separation system and converts the oxygenate contaminants to paraffins.

Another embodiment of the present invention is a method for hydrogenating oxygenates, including contacting in a hydrogenation unit an oxygenate in an oxygenate-containing MTO reactor effluent with hydrogen and a hydrogenation catalyst under conditions effective to convert the oxygenate to one or more paraffin compounds.

Optionally, the oxygenate-containing MTO reactor effluent of the inventive method or reactor system includes $C_4+$ and/or $C_5+$ olefin. The $C_4+$ or $C_5+$ olefin contacts hydrogen and the hydrogenation catalyst in the hydrogenation unit under conditions effective to convert the $C_4+$ or $C_5+$ olefin to one or more paraffin compounds.

BRIEF DESCRIPTION OF THE FIGURES

Various embodiments of the overall invention are shown by way of example in the attached Figures, wherein.

DETAILED DESCRIPTION

The present invention provides a practical use for oxygenate contaminants and/or heavy olefin contaminants in a product effluent. Specifically, the invention is a new method and reactor system for converting $C_4+$ or $C_5+$ oxygenate contaminants and/or $C_4+$ or $C_5+$ olefins (heavy olefins) separated from a product effluent to commercially useful hydrocarbons, e.g., paraffins. The invention is particularly well-suited for implementation in an oxygenate-to-olefin (OTO) reactor system such as an methanol-to-olefin (MTO) reactor system. Heavier oxygenates and/or heavy olefins preferably are separated from the product effluent through a bottoms stream of a quench tower. Additionally or alternatively, at least a portion of the lighter oxygenates and/or heavy olefins in the overhead stream of the quench tower are removed from the product effluent through a water absorption unit bottoms stream and/or by a separation unit, e.g., distillation unit, which optionally is downstream of the quench tower and the water absorption unit. The oxygenates and/or heavy olefins from the bottoms stream of the quench tower and/or from the water absorption unit and/or from the separation unit, e.g., distillation unit, preferably are directed, alone or in combination, to one or more hydrogenation units wherein the oxygenates and/or heavy olefins are hydrogenated over a catalyst, preferably a sulphided catalyst of the type Nickel or Cobalt combined with Molybdenum or Tungsten. Through hydrogenation, at least a portion of the oxygenates and/or heavy olefins are converted to hydrocarbons such as paraffins, which can be used in a variety of commercially viable applications. For example, the $C_5+$ paraffins can be used in blending motor fuels or as solvents or as steam cracking feed. $C_4$ and lower paraffins can be used as steam cracker feed or fuel, e.g., as LPG.

The product effluent from an MTO reactor contains many oxygenates. For example, an MTO product effluent can include one or more of the following oxygenates: Dimethyl Ether (DME), Methyl Ethyl Ether, Methyl Isopropyl Ether, Acetaldehyde, Methyl Sec-Butyl Ether, n-Propanal, 2-Propenal, 2-Methyl-2-Propenal, iso-Butanal, Butanal, Acetic Acid, Methyl Ester, Methanol, Acetone, 2-Methyl Butanal, Propanoic Acid, Methyl Ester, 3-Buten-2-one, Ethanol, 2-Butanone, iso-Propanol, 3-Methyl-3-Buten-2-one, Pentanal, 2-Methyl Pentanal, 3-Methyl Pentanal, 3-Methyl-2-Butanone, 3-Pentanone, 2-Methyl-1-Penten-3-one, 2-Pentanone, 2-Methyl-3-Pentanone, 3-Methyl-2-Pentanone, 4-Methyl-2-Pentanone, Formic Acid, Acetic Acid, Propanoic Acid, and Butyric Acid.

Additionally, an MTO product effluent can include one or more olefins. For example, an MTO product effluent can include one or more of the following olefins: acetylene, ethylene, propylene, 1-butene, 2-butene, isobutene, butadiene, $C_5$ olefins, $C_5$ diolefins, $C_6$ olefins, and $C_7+$ olefins. In accordance with the present invention, one or more of these oxygenates and/or olefins are converted in a hydrogenation unit to one or more paraffin compounds. Preferably, the catalyst used in the hydrogenation unit is a sulfided catalyst, however, any hydrogenation catalyst could be implemented in accordance with the present invention.

In accordance with the present invention, one or more oxygenate-containing streams from an MTO system are directed to a hydrogenation unit. Preferably, the oxygenate-containing stream is selected from one or more of the following: the bottoms stream from a quench tower, the bottom stream from a water absorption unit, a $C_4+$ stream, and/or a $C_5+$ stream. These streams, alone or in combination, can contain from 0.2 to 1.4, 0.5 to 1.4, or 0.75 to 1.4 weight percent alcohols (excluding methanol); from 0.0006 to 0.1, 0.005 to 0.1, or 0.01 to 0.1 weight percent ethers (excluding DME); from 0.1 to 12.0, 1.0–12.0, or 5.0– 12.0 weight percent aldehydes; from 1.0 to 41.0, 10.0 to 41.0, or 20.0 to 41.0 weight percent ketones; and/or from 0.001 to 0.050, 0.015 to 0.050, or 0.030 to 0.050 weight percent esters. The ranges provided are on a dry basis. Preferably, the one or more oxygenate-containing streams from an MTO system that are directed to a hydrogenation unit comprise at least 5, 15, 25, 40 or 50 weight percent oxygenates. The $C_4+$ and $C_5+$ streams preferably include, respectively, $C_4+$ and $C_5+$ olefins as well as oxygenates which codistil in the separation units of the MTO plant.

The hydrogenation unit preferably contains a hydrogenation catalyst. Hydrogen is directed to the hydrogenation unit and contacts one or more oxygenates under conditions effective to hydrogenate the oxygenates thereby forming a hydrocarbon-containing stream. Preferably, the oxygen from the oxygenate compounds is converted in the presence of hydrogen to water which can be removed from the hydrocarbon-containing stream through well-known separation techniques. For example, water byproduct can be separated from the hydrocarbons in a downstream distillation facility.

Additionally or alternatively, the hydrogen contacts one or more olefins under conditions effective to hydrogenate the olefins. Thus, additionally or alternatively, the stream from the MTO system which is directed to the hydrogenation unit contains olefins, preferably $C_4+$ olefins or $C_5+$ olefins. Optionally, the stream which is directed from the MTO system to the hydrogenation unit can contain both oxygenates and olefins.

Conventional hydrogenation processes can be used in accordance with the present invention. For example, numerous references are provided in *Sulphide Catalysts: Their Properties & Applications* by Weisser & Landa (Pergamon Press), which is incorporated herein by reference. See, particularly, pages 150–178 thereof regarding oxygenate hydrogenation.

In another reference, U.S. Pat. No. 3,363,009 to Pine & Ellert, the entirety of which is incorporated herein by reference, the design of a molybdenum sulphide catalyst was provided wherein the aim was to stop ketone hydrogenation at the alcohol stage to avoid production of paraffins. In this case, no nickel or cobalt was added to the catalyst formulation and activated carbon rather than alumina was used as support.

Such catalysts as Co/Mo, Ni/Mo etc. have been widely described in the treatment of petroleum cuts in British Patent No. 1,122,716 to Shell, which is incorporated herein by reference. See also U.S. Pat. No. 3,363,009, incorporated herein by reference, which provides for tallow hydrogenation with a nickel/tungsten catalyst. Treatment of heavy fractions uses similar catalysts. See, e.g., U.S. Pat. No. 3,649,525, incorporated herein by reference, describing the use a Ni/Mo catalyst for heavy residual oils. Such fractions contain significant oxygenated as well as sulphur-containing hydrocarbons. Sulphur is easy to determine analytically whereas oxygen is more difficult. Thus, all work on treatment of these heavy cuts centers on the ability to remove sulphur. The oxygen is also removed by a similar chemical process, although data are rarely provided.

In one embodiment, the process of the invention utilizes an adaptation of a hydrodesulphurization catalyst in which nickel and/or cobalt and either molybdenum or tungsten are impregnated as their respective oxides onto an alumina support, preferably of high surface area alumina, e.g., gamma alumina or alumina spinel, e.g., nickel spinel having the requisite pore volume. The preferred components are nickel and tungsten on a gamma alumina support. The concentration of metals on the catalyst is important for good performance and ranges from 2 to 10, preferably 4 to 5, weight percent nickel and from 10 to 25, preferably 16 to 20, weight percent tungsten. The catalyst support can contain silica up to a concentration wherein the catalytic surface activity is not markedly affected.

Preferably, the oxygenate and/or heavy olefin is passed with an excess of hydrogen or hydrogen rich gas over a hydrogenation catalyst. The catalyst preferably is a sulfided nickel tungsten or nickel molybdenum catalyst on an alumina support having a specific fresh surface area ranging from 120–300 m$^2$/g and containing from 2 to 10% by weight nickel and from 10 to 25% by weight tungsten, or from 2 to 10% by weight nickel and from 10 to 25% by weight molybdenum.

Optionally, the hydrogenation catalyst is supported by high surface area gamma alumina supports having a fresh catalyst surface area ranging from 150–240 m$^2$/g. The catalyst preferably contains about 4% weight nickel and 12 to 20% weight molybdenum or tungsten. Sulfides of molybdenum and tungsten without the use of nickel promoters also can be implemented in accordance with the present invention but are more difficult to sulphide in situ. For the formerly described catalysts which are on high surface area gamma alumina supports, one would expect higher activities or the need for milder conditions, particularly pressure. Nickel/tungsten tend to perform better than nickel/molybdenum and better than cobalt/molybdenum in accordance with the present invention.

In one embodiment, the hydrogenation catalyst comprises a sulphide of a Group VIII metal, such as nickel or cobalt, with a Group VIB metal, such as molybdenum and/or tungsten, impregnated onto a porous support, such as gamma alumina. Such catalysts, particularly nickel-tungsten sulphide are capable of hydrogenating a variety of oxygenated hydrocarbons to their corresponding paraffin. These catalysts also are capable of hydrogenating olefins and aromatics to paraffins.

The hydrogenation process preferably occurs in a fixed bed downflow reactor operating at greater than 50 bar and preferably between 100 and 200 bar and at a temperature range of 150–350° C., more preferably 180–350° C., and most preferably 200–330° C. The resulting mixture of paraffins in the $C_5$–$C_{10}$ range is suitable as a motor gasoline blendstock. Also, this hydrogenation process simplifies the recovery stream and decreases the recycle of undesirable oxygenated hydrocarbons to the MTO reactor. Under optimized conditions, alcohols, ethers, esters, aldehydes and ketones are converted to paraffins. The above-described catalysts are also particularly effective for hydrogenating olefins to form paraffins. For example, butanol is converted to butane, acetone to propane, ethyl propionate to ethane and propane.

In one embodiment, the one or more feed streams that are directed to the hydrogenation facility originate from the compression, washing and distillation of an MTO reactor effluent. In this embodiment, the feed stream comprises C4+ or C5+ hydrocarbons and oxygenates. Additionally or alternatively, the feed stream comprises a heavy oxygenate concentrate from which DME and methanol have been removed. Optionally, this concentrated stream is derived from distillation or stripping of the combined quench/water wash process streams.

A preferred non-limiting separation system, which can be implemented in the present invention, will now be described in more detail. In one embodiment, the invention is coupled with a method for removing oxygenated components such as methanol and DME from an effluent stream. The separation system provided is particularly beneficial for removing DME from an ethylene and/or propylene stream so that the ethylene and/or propylene can be polymerized without poisoning catalyst used in the polymerization reaction. These light oxygenates can be hydrogenated or recycled as feedstock to the MTO reactor. However, it is desirable to remove such components prior to hydrogenation since the hydrogenation of DME and methanol yields methane which is not a particularly valuable hydrocarbon. For this reason, the feed stream that is directed to the hydrogenation unit should be treated to reduce, preferably eliminate, the amount of DME and methanol that enters the reactor system. Similarly, $C_3$– olefins and oxygenates preferably are not directed to the hydrogenation unit because the hydrogenation of these compounds also yields undesirable methane.

In this invention, oxygenated contaminants, particularly including DME, are removed from the provided olefin stream at low or high pressure. An advantage of using a low pressure separation is that lower temperatures can be obtained in the heavier fractions separated during the separation process. A benefit of lower temperatures is that there will be fewer equipment fouling problems. In addition, such a process will use a lower energy input to run associated operating equipment such as reboilers and condensers.

Another advantage in low pressure separation is that less energy will be required to maintain system separation pressure. This means that compressors having fewer stages can be more readily utilized.

An advantage of using a high pressure separation is that separation of olefins can be accomplished at higher temperatures. By taking advantage of higher temperature separation, less refrigeration is required to recover lighter olefins such as ethylene and propylene. The practical result is a substantial savings in energy.

Another advantage of high pressure separation is that clathrate and free water formation can be more easily controlled in the separation equipment. This is particularly advantageous when distillation columns having internal trays are used as the separation equipment, since internal trays are prone to collect water and clathrates. If an excessive amount of water and/or clathrates are collected, the trays can break apart or collapse, causing severe equipment damage.

In general, the method of separating DME from an ethylene/propylene stream at low pressure comprises providing an olefin stream which contains ethylene, ethane, propylene, propane, and DME, then separating at least a majority, i.e., greater than 50%, of the DME present in the olefin stream. The olefin stream can come from any conventional source. However, this method is particularly effective in separating DME from olefin streams made from an oxygenate to olefin process.

In one embodiment of the exemplary removal method, the olefin stream that is provided comprises not greater than about 50 wt % DME, preferably not greater than about 20 wt % DME, more preferably not greater than about 10 wt % DME, and most preferably not greater than about 5 wt % DME. Of course, for DME to be removed from the olefin stream, some measurable amount must be present. Desirably, the provided olefins stream will contain at least about 100 wppm DME, preferably at least about 500 wppm DME, and more preferably at least about 1,000 wppm DME.

In another embodiment of the DME removal method, the olefin stream that is provided comprises at least about 25 wt % ethylene. Preferably, the provided olefin stream comprises from about 25 wt % ethylene to about 75 wt % ethylene, more preferably from about 30 wt % to about 60 wt %, and most preferably from about 35 wt % to about 50 wt % propylene.

In another embodiment, the olefin stream that is provided also comprises at least about 20 wt % propylene. Preferably, the provided olefin stream comprises from about 20 wt % propylene to about 70 wt % propylene, more preferably from about 25 wt % to about 50 wt % propylene, and most preferably from about 30 wt % to about 40 wt % propylene.

It is desirable that the provided olefin stream contain a relatively low concentration of ethane, preferably a lower concentration of ethane than propane. Preferably, the olefin stream comprises not greater than about 4 wt % ethane, more preferably not greater than about 3 wt % ethane, and most preferably not greater than about 2 wt % ethane.

It is also desirable that the provided olefin stream contain a relatively low concentration of propane. Preferably, the olefin stream comprises not greater than about 5 wt % propane, more preferably not greater than about 4 wt % propane, and most preferably not greater than about 3 wt % propane.

In another embodiment of the DME removal method, the provided olefin stream contains both ethylene and propylene. Desirably, the olefin stream contains at least about 50 wt % ethylene and propylene. Preferably, the olefin stream contains from about 50 wt % to about 95 wt % ethylene and propylene, more preferably from about 55 wt % to about 90 wt % ethylene and propylene, and most preferably from about 60 wt % to about 85 wt % ethylene and propylene.

The provided olefin steam can also contain some amount of water. However, it is desirable that any water present in the olefin stream will be at a concentration such that free water formation (i.e., formation of a separate water phase) or gas hydration does not significantly impede the separation process. Gas hydration results in the formation of a clathrate compound. Clathrate compounds are solids, and are essentially insoluble in water and hydrocarbons. Such compounds can cause significant problems in the separation process.

Water that is present in the provided olefin stream should be at a concentration sufficiently low such that a separate water phase is not formed during the separation process. This is particularly important when a distillation column having trays is used to separate the DME from the olefin, since a separate water phase formed in the trays will impede mass transfer and add extra weight to each tray. Distillation columns having packing are preferred at higher concentrations of water, since such as column will not have trays to hold up separate water phases.

It is desirable in this separation system that the provided olefin stream contain not greater than about 15,000 wppm water. Preferably the olefin stream contains not greater than about 10,000 wppm water, more preferably not greater than 5,000 wppm water, and most preferably not greater than about 1,000 wppm water.

It is not necessary in this invention that the olefin stream be completely dry. That is, the olefin stream can contain some water. The benefit of the olefin stream containing some amount of water is that additional and/or complex drying equipment will not be needed before separating the DME from the olefin stream. In the low pressure separation embodiment, the olefin stream preferably contains at least about 10 wppm water, more preferably at least about 20 wppm water, and most preferably at least about 25 wppm water.

The high pressure separation embodiment can tolerate more water than the low pressure separation. In the high pressure separation embodiment, the olefin stream preferably contains at least about 10 wppm water, more preferably at least about 100 wppm water, and most preferably at least about 200 wppm water.

If an olefin stream contains an unacceptably high concentration of water, a sufficient amount of the water can be removed either prior to or during separation of the DME using a water absorbent. Examples of water absorbents include alcohols, amines, amides, nitriles, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

To obtain a substantial degree of effectiveness, the water absorbent should contain little non-water absorbing components. For example, the water absorbent should contain at least about 75 wt % water absorbing components. Desirably, the water absorbent contains at least about 90 wt %, preferably at least about 95 wt %, and most preferably at least about 98 wt % water absorbent.

When a water absorbent is used to reduce the concentration of water in the olefin stream prior to separation of the DME, a wash type of process using a wash vessel can be used. In essence, a wash process is one in which the olefin stream is contacted with water absorbent such that a substantial amount of the water is removed, i.e., washed out, from the olefin stream. The amount of absorbent added to the wash vessel should be sufficient to substantially reduce free water formation (i.e., formation of a separate liquid phase), particularly in the vessel in which the separation of the DME from the olefin takes place. In this embodiment, it is desirable that water absorbent be added to the wash vessel at a mole ratio of absorbent compound to total olefin feed to the wash vessel of about 1:2 to about 1:200. Preferably, the absorbent is added at a mole ratio of from about 1:5 to about 1:100, and more preferably from about 1:10 to about 1:50.

Although the olefin stream can come from any conventional source which contains DME, the invention is particularly suited to removing DME from olefin streams made from an oxygenate to olefin process. In one embodiment of this invention, an olefin stream containing DME is obtained by contacting oxygenate feedstock with a molecular sieve catalyst.

In a preferred embodiment of the process of the invention, the oxygenate feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

Molecular sieves capable of converting an oxygenate to an olefin compound include zeolite as well as non-zeolite molecular sieves, and are of the large, medium or small pore type. The small, medium and large pore molecular sieves have from a 4-ring to a 12-ring or greater framework-type. In a preferred embodiment, the molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Åmore preferably from 3 Å to about 4.5 Å, and most preferably from 3.5 Å to about 4.2 Å. The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves.

Non-limiting examples of SAPO and ALPO molecular sieves used in the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. In an embodiment, the molecular sieve is an intergrowth material having two or more distinct phases of crystalline structures within one molecular sieve composition.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796; U.S. Pat. No. 6,287,522 (dual riser); *Fluidization Engineering*, D. Kunii and O. Levenspiel, Robert E. Krieger Publishing Company, New York, N.Y. 1977; and *Riser Reactor, Fluidization and Fluid-Particle Systems*, pages 48 to 59, F. A. Zenz and D. F. Othmer, Reinhold Publishing Corporation, New York, 1960; U.S. Pat. No. 6,166,282 (fast-fluidized bed reactor), and U.S. patent application Ser. No. 09/564,613 (multiple riser reactor), which are all herein fully incorporated by reference, which are all herein fully incorporated by reference.

The conversion temperature employed in the conversion process, specifically within the reactor system, is in the range of from about 200° C. to about 1,000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, is not critical. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kpaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and DME is in the range of from about 20 $hr^{-1}$ to about 300 $hr^{-1}$. See for example U.S. Pat. No. 5,952,538, which is herein fully incorporated by reference.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

The oxygenate to olefin process forms a substantial amount of water as a by-product. Much of this water can be removed by cooling the olefin stream from the oxygenate reactor to a temperature below the condensation temperature of the water in the stream. Preferably, the temperature of the product stream is cooled to a temperature below the condensation temperature of the oxygenate feed for the oxygenate to olefins process. In certain embodiments, it is desirable to cool the product stream below the condensation temperature of methanol.

A quench tower or column is one type of equipment that is effective in cooling the olefin stream from the oxygenate to olefin reaction process. In a quench column, a quenching fluid is directly contacted with the olefin stream to cool the stream to the desired condensation temperature. Condensation produces a condensed water-containing stream, which generally exits the quench column as a bottoms stream. Olefin generally exits the column as an overhead stream. The overhead stream contains DME which must be separated according to this invention. If a high concentration of water still remains in the overhead, then absorbents can be used as described above to lower the water concentration further. The quench column bottoms stream also contains oxygenate contaminants which optionally are to be hydrogenated to form paraffins in accordance with the present invention.

In one particular embodiment of the invention, the quenched olefin stream is further processed by compression, preferably multi-staged compression. Two, three, four or more stages can be used, with two or three stages being preferred.

During or after multi-stage compression, the olefin stream can be washed using a water absorbent, as described above, if desired. This wash using water absorbent can mitigate problems related to gas hydration and/or separate water phase formation. Preferably, multi-stage compression using a water absorbent wash between stages is preferred. The bottoms stream from the water absorption unit also contains oxygenate contaminants which can be hydrogenated to form paraffins in accordance with the present invention. The DME and $C_4+$ hydrocarbon components are then separated from the olefin stream.

In one embodiment of this invention, the olefin stream is separated into a first fraction and a second fraction, with a majority of ethylene and/or propylene being separated in the first fraction and a majority of the DME being separated in the second fraction. In one embodiment, the separation is carried out at a pressure of less than 200 psig (1,480 kPa absolute). Preferably, separation is carried out at a pressure of from about 100 psig (791 kPa absolute) to about 200 psig (1,480 kPa absolute), more preferably from about 120 psig (929 kPa absolute) to about 180 psig (1,342 kPa absolute). Higher pressures can also be used as disclosed above.

As indicated above, the separation can be performed at a high pressure. For example, in the high pressure separation embodiment, the olefin stream can be separated into a first fraction and a second fraction at a pressure of at least about 200 psig (1,480 kPa absolute). Preferably, the high pressure separation is carried out at a pressure of from about 200 psig (1,480 kPa absolute) to about 290 psig (2,100 kPa absolute), more preferably from about 250 psig (1,825 kPa absolute) to about 290 psig (2,100 kPa absolute).

In the high pressure separation embodiment, the actual upper pressure limit of the separation process will typically depend upon the temperature at which the second fraction is separated. The second fraction will contain DME and other hydrocarbons having boiling points higher than DME, for example $C_4+$ olefins. It is desirable to keep the compounds in the second fraction sufficiently low in temperature so as not to cause chemical degradation or fouling problems in other downstream separation and treating equipment.

In this embodiment, separation will be such that the second fraction will have an average temperature of not greater than about 250° F. (121° C.), preferably not greater than about 240° F. (116° C.), and more preferably not greater than about 230° F. (110° C.).

In another embodiment of the invention, the separation process is performed in a-distillation column such that the first or overhead stream is at a temperature of not greater than about 30° F. (−1.1° C.). Preferably the first or overhead stream is at a temperature of about 0° F. (−17.8° C.) to about 30° F. (−1.1° C.), more preferably about 10° F. (−12.2° C.) to about 25° F. (−3.9° C.).

It is desirable in this invention that the second or bottoms fraction of the distillation column be maintained at a temperature level to reduce fouling problems. In one embodiment, the second fraction is at an average temperature of not greater than about 210° F. (99° C.), preferably not greater than about 200° F. (93° C.), and more preferably not greater than about 190° F. (88° C.).

It is further desirable in this invention that water absorbent, as described above, be added to the vessel in which the separation of the oxygenated contaminants from the provided olefin stream is performed. The addition of water absorbent directly to the separation vessel can be of additional benefit in reducing free water and/or clathrate formation in the vessel.

In one embodiment of the invention, water absorbent is added to the oxygenate separation vessel in an amount sufficient to substantially reduce oxygenate content (e.g., DME) or clathrate formation. It is preferred that water absorbent be added to the vessel at a molar ratio of water absorbent to total olefin feed entering the separation vessel of about 4:1 to about 1:5,000. Higher molar ratios of water absorbent to total olefin feed are desirable for reducing oxygenate content; preferably from about 4:1 to about 1:1, more preferably from about 3:1 to about 1.2:1, and most preferably from about 2.5:1 to about 1.5:1. Lower molar ratios of water absorbent to total olefin feed are desirable for reducing clathrate formation; preferably from about 1:1 to about 1:5,000, more preferably from about 1:100 to about 1:4,000, and most preferably from about 1:500 to about 1:3,000.

In one embodiment of this invention, separation is by conventional distillation. Distillation is carried out using a vessel or tower having internal packing or trays that creates a temperature difference from top to bottom of the tower. The upper portion of the tower is the cooler portion, and higher volatile components in the feed exit from the top of the tower.

In this invention it is desirable to obtain high concentrations of ethylene and propylene from an olefin stream containing DME. In one embodiment, the DME is separated from the ethylene and propylene in the olefin stream. In this embodiment the ethylene and propylene are recovered in a first fraction, and the DME is recovered in a second fraction. Typically, the first fraction will be the overhead or side fraction of a distillation column, and the second fraction will be a bottoms fraction or additional side fraction of a distillation column.

In one embodiment of the invention, a majority of the ethylene and propylene in the provided olefin stream will be separated in a first fraction and a majority of the DME and other oxygenates in the provided olefin stream will be separated in a second fraction. Preferably, the first fraction will contain at least about 75% of the ethylene and propylene in the provided olefin stream, more preferably at least about 85%, and most preferably at least about 95%.

In another embodiment, at least about 75% of the DME in the provided olefin stream will be separated out in the second fraction. Preferably, at least about 85% of the DME in the provided olefin stream will be separated out in the second fraction, more preferably at least about 95%, and most preferably at least about 99%.

A majority of the propane in the provided olefin stream can be separated out in either the first or second fraction. If the majority of the propane is contained in the first fraction, then there will be less separation of heavier products needed in the second fraction. However, there can be slightly increased levels of DME in the first fraction when a majority of the propane is in the first fraction. In this embodiment, at least about 60% of the propane in the provided olefin stream, preferably at least about 70%, and more preferably at least about 80% will be in the first fraction, and the first fraction will contain not greater than about 50 wppm, preferably not greater than about 25 wppm, more preferably not greater than about 10 wppm DME, and most preferably not greater than about 5 wppm DME.

If a majority of the propane in the provided olefin stream is separated out in the second fraction, then the concentration of DME in the first fraction will be significantly lower. In this embodiment, at least about 60% of the propane in the provided olefin stream, preferably at least about 70%, and more preferably at least about 80% will be in the second fraction, and the second fraction will contain not greater than about 25 wppm, preferably not greater than about 15 wppm, more preferably not greater than about 5 wppm ether, and most preferably not greater than about 1 wppm DME.

In another embodiment of the invention, the second fraction will also contain some hydrocarbon compounds having four or more carbons. These compounds are also known as $C_4+$ components. The amount of $C_4+$ components in the second fraction can vary, particularly depending upon the amount of propane in the second fraction. For example the second fraction can contain from about 5 wt % to about 90 wt % $C_4+$ components. Preferably, the second fraction contains from about 25 wt % to about 80 wt % $C_4+$ components, more preferably from about 35 wt % to about 75 wt % $C_4+$ components.

It is of further advantage in this invention to operate the separation vessel at a temperature and pressure to separate out of the provided olefin stream at least a majority (i.e., at least 50%) of any propadiene which might be present. In this embodiment, the propadiene would preferably be separated out in the second fraction along with DME. Preferably, at least about 75%, more preferably at least about 85%, and most preferably at least about 95% of the propadiene would be separated out. Separating out any propadiene in this manner would necessarily include separating out a substantial portion of any methyl acetylene which can also be present in the provided olefin stream. This is because methyl acetylene has a lower normal boiling point than propadiene and DME. Removing propadiene and methyl acetylene from the provided olefin stream would provide a substantial benefit in that the first fraction containing the ethylene and/or propylene would have a very high concentration of mono-olefinic compounds. Such a stream would need little if any hydro processing, which might typically be needed to reduce the number of diolefins or alkylene compounds recovered in the first fraction.

This separation technique is particularly advantageous for treating the ethylene and propylene streams contained in the first fraction to remove entrained acid gases such as $CO_2$ which can also be present in such fraction. The advantage is that in this invention the separated ethylene and propylene streams will contain relatively few hydrocarbon components that cause fouling problems in such acid gas treatment systems.

Solid or liquid acid gas treatment systems can be used in this invention. In either system, the acid gas is removed from the ethylene and/or propylene stream in the first fraction by contacting the first fraction with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an olefin stream. Examples of such alkaline compounds include sodium hydroxide and potassium hydroxide.

Following acid gas treating, it is desirable to remove additionally entrained material in the treated ethylene and/or propylene using a water wash. Conventional equipment can be used. It is desirable, however, to further remove additional water from the separated ethylene and/or propylene streams.

In one embodiment of this separation technique, the ethylene and propylene in the first fraction is water washed, i.e., contacted with a water stream, prior to acid gas treating. This contacting is particularly advantageous when water absorbent is added to the oxygenate separation vessel, as water absorbent can carry over into the first or overhead fraction. Water washing would then be conducted to remove a substantial portion of water absorbent carry over prior to acid gas treating.

This invention further includes an optional drying embodiment. In this embodiment, a solid or liquid drying system can be used to remove water and/or additional oxygenated hydrocarbon from the first fraction.

In the solid drying system, the ethylene and/or propylene having been separated in a first fraction, and optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that are not normally removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3 Å molecular sieves, 4 Å molecular sieves, and alumino-silicates. Beds containing mixtures of these sieves or multiple beds having different adsorbent solids can be used to remove water, as well as a variety of oxygenated hydrocarbons.

In this separation technique, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3 Å molecular sieve. This bed is then followed by one or more beds containing one or more less selective adsorbents such as a larger pore molecular sieve e.g. 13× and/or a high surface area active alumina such as Selexorb CD (Alcoa tradename).

In another embodiment, the first bed is a 3.6 Å molecular sieve capable of selectively removing both water and methanol. This bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably, the water absorbent is the same as that previously described.

Preferably the olefin from the adsorption beds contains less than about 100 wppm water, more preferably less than about 10 wppm, and most preferably less than 1 wppm. Preferably less than about 10 wppm DME is present in the stream leaving the adsorption beds, more preferably less than about 5 wppm, and most preferably less than about 1 wppm.

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives can be formed from the ethylene, propylene and $C_4+$ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl chloride, ethylbenzene, ethylene oxide, cumene, acrolein, allyl chloride, propylene oxide, acrylic acid, ethylene-propylene rubbers, and acrylonitrile, and trimers and dimers of ethylene and propylene. The $C_4+$ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

Figure 1:
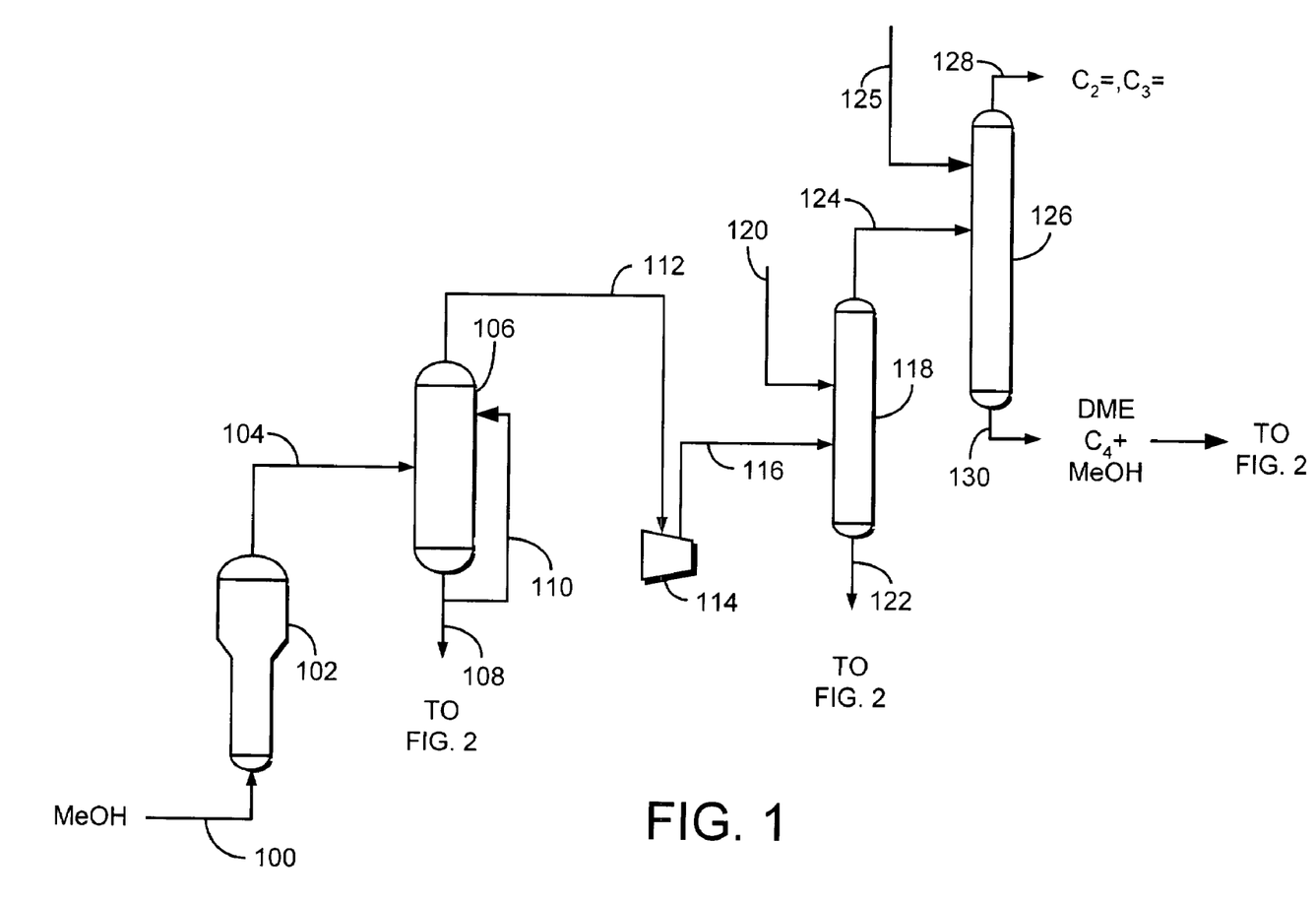
FIG. 1 is a flow diagram showing a process for reacting methanol to form an olefin, with the olefin being separated into a first fraction containing ethylene and propylene and a second fraction containing dimethyl ether and $C_4+$ hydrocarbon components.

One example of separating DME from an olefin stream is shown in FIG. 1. This example demonstrates one way of obtaining an ethylene and propylene stream substantially depleted of DME, as well as $C_4$+ components. The common factor in this invention, however, is that the DME and $C_4$+ components are substantially removed from the ethylene and/or propylene containing stream prior to caustic treatment. This means that both ethylene and propylene can be recovered in a first fraction, with the DME and $C_4$+ components being recovered in a second fraction. Propane which is present in the olefin stream can be recovered in either the first or second stream, depending upon how low a concentration of DME in the first fraction is desired. The ethylene and propylene can then both can be recovered and further treated, e.g., caustic wash treated or water wash treated, together or separated and treated separately.

FIG. 1 shows one embodiment of the present invention in which the oxygenate contaminants and olefins to be treated in the hydrogenation unit are made in an oxygenate to olefin reaction system. In the Figure, methanol is sent through line 100 to an oxygenate to olefin reactor 102 where the methanol is converted to an olefin-containing stream comprising methane, ethylene, ethane, propylene, propane, DME, $C_4$+ components, water and other hydrocarbon components. The olefin-containing stream is sent through a line 104 to a quench tower 106 where the olefin is cooled and water and other condensable components are condensed.

The condensed components, which comprise a substantial amount of water, are withdrawn from the quench tower 106 through a bottoms line 108. A portion of the condensed components are recycled through a line 110 back to the top of the quench tower 106. The line 110 contains a cooling unit, e.g., heat exchanger, (not shown) to further cool the condensed components so as to provide a cooling medium to further cool the components in quench tower 106.

Olefin vapor leaves through the overhead portion of quench tower 106 through line 112. The olefin vapor is compressed in one or more compressors 114 and the compressed olefin is passed through line 116 to a water absorption unit 118. Methanol is preferably used as the water absorbent, and is fed to the top portion of the water absorption unit 118 through line 120. Methanol and entrained water, as well as some oxygenated hydrocarbon, is separated as a bottoms stream though line 122. Olefin is recovered through overhead line 124. Optionally, the olefin is sent to an additional compressor(s) (not shown), and then is input to a distillation column 126.

The distillation column 126 separates ethylene and propylene, as well as lighter boiling point components from the DME and heavier components, including $C_4$+ components, unreacted methanol, and methanol remaining from the methanol wash. Additional methanol optionally is added to the distillation column 126 though line 125 to reduce clathrate and/or free water formation in the distillation column. The ethylene and propylene containing stream exits the distillation column 126 through overhead line 128, and the heavier components which include the DME and $C_4$+ components exit the distillation column 126 through bottoms line 130. Line 128 can be directed to a caustic wash unit, a water wash column, and/or a drying unit.

Optionally, bottoms line 130 is directed to one or more water wash columns and/or separation unit(s). In one embodiment, the separation unit(s) separate $C_4$ compounds from $C_5$+ compounds. Either or both the $C_4$ and/or $C_5$+ streams can then be directed to, and optionally combined with, stream 200 of FIG. 2.

Figure 2:
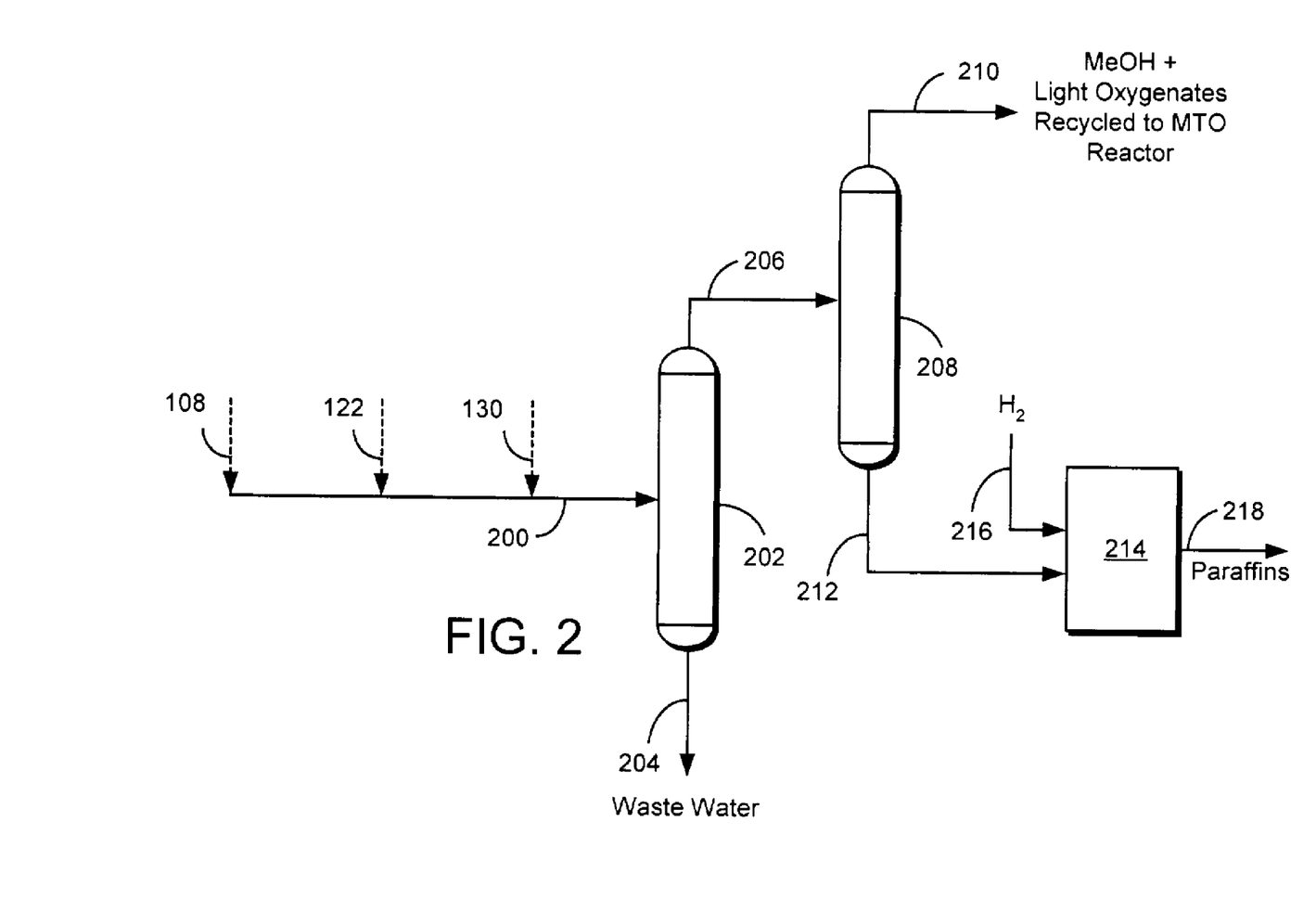
FIG. 2 is a flow diagram showing a process for removing water from an oxygenate-containing stream and separating the light oxygenates from the heavy oxygenates, and hydrogenating the heavy oxygenates to form hydrocarbons.

In one embodiment of the present invention, bottoms line 108 from the quench tower 106 is directed by line 200 to a water removal unit or water stripper 202 as shown in FIG. 2. The water stripper removes waste water through waste bottoms stream 204. Water is removed in the water stripper as condensation while a light oxygenate-containing stream is removed through overhead line 206. In one embodiment, line 206 is then directed to a separation unit as shown by distillation column 208. The overhead stream 210 from the separation unit 208 preferably contains methanol, DME and, optionally, other light oxygenates. The methanol, DME, and/or other light oxygenates optionally are redirected to the oxygenate to olefin reactor 102 for further conversion to light olefins. For example, overhead light oxygenate-containing stream 210 could be directed to and optionally combined with methanol-containing line 100. Additionally or alternatively, the light oxygenate-containing overhead stream 210 from separation unit 208 is sent directly to the oxygenate-to-olefin reactor 102.

Bottoms stream 212 from separation unit 208 preferably contains $C_4$+ oxygenates and/or $C_4$+ olefins. Alternatively, the separation unit 208 is designed so that $C_5$+ olefins and/or $C_5$+ oxygenates are contained in bottoms stream 212. In this embodiment, overhead stream 210 includes $C_4$– oxygenates and/or $C_4$– olefins. In either embodiment, bottoms stream 212 is directed to hydrogenation unit 214. The hydrogenation unit preferably contains a hydrogenation catalyst, e.g., a sulfide hydrogenation catalyst. Hydrogen is introduced into hydrogenation unit 214 as shown by hydrogen introduction line 216. In the hydrogenation unit, hydrogen from line 216 contacts oxygenates and/or olefins from line 212 and the hydrogenation catalyst under conditions effective to convert at least a portion of the oxygenates and/or olefins from line 212 into paraffins. The paraffins are then removed from hydrogenation unit 214 as shown by paraffin removal line 218.

In another embodiment of the present invention, a plurality of hydrogenation units are implemented in parallel or in series. For example, in one embodiment, oxygenate-containing and olefin-containing line 212 optionally is directed to an oxygenate-olefin separation unit. In the oxygenate-olefin separation unit, the oxygenates from line 212 and the olefins from line 212 can be separated from each other. Subsequently, the oxygenate stream from the oxygenate-olefin separation unit can be directed to an oxygenate hydrogenation unit which in one embodiment contains a catalyst specifically selected for hydrogenation of oxygenates. Similarly, the olefins stream from the oxygenate-olefin separation unit can be directed to an olefin hydrogenation unit which can contain an olefin hydrogenation catalyst specifically selected for its hydrogenation properties of olefins. By directing separate oxygenate-containing and olefin-containing streams to separate hydrogenation units which contain catalysts specifically selected for the hydrogenation properties of their respective oxygenate or olefin feedstocks, increased paraffin conversion can be obtained.

In another embodiment, the olefin hydrogenation unit and oxygenate hydrogenation unit can be connected in series. In this embodiment, oxygenate-containing and olefin-containing stream 212 can be directed to the oxygenate hydrogenation unit first, wherein at least a portion of oxygenates are converted to paraffins over an oxygenate hydrogenation catalyst. Subsequently, the hydrogenation effluent from the oxygenate hydrogenation unit can be directed to an olefin hydrogenation unit which preferably contains an olefin hydrogenation catalyst, such as a nickel, platinum and/or palladium catalyst adsorbed on a carbon support. In the olefin hydrogenation unit, the olefins are converted to paraffins. In another embodiment, the olefin hydrogenation unit can be upstream of the oxygenate hydrogenation unit.

Other catalysts have activity for hydrogenation of oxygenates, for example, from carbonyl compounds to alcohols. Some of these catalysts can, under sufficient temperature and pressure, hydrogenate the oxygenates to paraffins. However, the present invention addresses, in one embodiment, hydrogenating a mixture of oxygenates, e.g., acids, esters, ethers, alcohols, ketones, and aldehydes, while avoiding extensive hydrogenation of the olefins in the $C_4+$ stream. For instance, platinum and palladium catalysts can split ethers and hydrogenate ketones to alcohols and even paraffins under more severe conditions. However, at these severe conditions, the $C_4+$ olefins would be totally saturated before significant oxygenate hydrogenation would occur. Thus, as discussed above, specialized oxygenate hydrogenation catalysts that do not facilitate saturation of the $C_4+$ olefins are particularly desirable in accordance with this embodiment of the present invention.

Having now fully described this invention, it will be appreciated by those skilled in the art that the invention can be performed within a wide range of parameters within what is claimed, without departing from the spirit and scope of the invention.

The invention claimed is:

1. A method for hydrogenating one or more of DME and $C_4+$ components from an oxygenate to olefin reactor system to form paraffins, comprising:

(a) providing an effluent stream from an oxygenate to olefin reactor system, wherein the effluent stream comprises ethylene, propylene, DME, and $C_4+$ components;

(b) separating the DME and $C_4+$ components from the ethylene and propylene;

(c) caustic treating the separated ethylene and propylene; and (d) hydrogenating at least a portion of the separated DME and $C_4+$ components, wherein the hydrogenating includes contacting at least a portion of the separated DME and $C_4+$ components with hydrogen and a catalyst to form paraffins.

2. The method of claim 1, wherein the catalyst includes Tungsten.

3. The method of claim 1, wherein the catalyst includes Nickel.

4. The method of claim 1, wherein the catalyst includes Molybdenum.

5. The method of claim 1, wherein the catalyst includes Cobalt.

6. The method of claim 1, wherein the separating occurs in a quench tower.

7. The method of claim 1, wherein the separating occurs in a water absorption unit.

8. The method of claim 1, wherein the separating occurs in a distillation unit.

* * * * *